United States Patent [19]

Sheppard et al.

[11] Patent Number: 5,126,273
[45] Date of Patent: Jun. 30, 1992

[54] MONITORING METHOD FOR THE SYNTHESIS OF A LINEAR CONBINATION OF AMINO ACID RESIDUES

[75] Inventors: Robert Sheppard, Cambridge, England; Morten Meldahl, Målov, Denmark

[73] Assignee: Novobiochem AG, Switzerland

[21] Appl. No.: 124,104

[22] PCT Filed: Feb. 3, 1987

[86] PCT No.: PCT/GB87/00078

§ 371 Date: Feb. 8, 1988

§ 102(e) Date: Feb. 8, 1988

[87] PCT Pub. No.: WO87/04713

PCT Pub. Date: Aug. 13, 1987

[30] Foreign Application Priority Data

Feb. 3, 1986 [GB] United Kingdom ............... 8602586

[51] Int. Cl.$^5$ .............................................. C07K 1/08
[52] U.S. Cl. ..................................... 436/89; 436/164; 436/166; 436/172; 530/333; 530/337
[58] Field of Search ................. 436/89, 90, 164, 166, 436/172, 86; 530/333, 334, 337

[56] References Cited

U.S. PATENT DOCUMENTS

| | | |
|---|---|---|
| 3,795,666 | 3/1974 | Konig et al. |
| 3,872,074 | 3/1975 | Konig et al. |
| 4,108,846 | 8/1978 | Meienhofer ........................ 530/334 |
| 4,192,798 | 3/1980 | Verlander et al. |
| 4,242,507 | 12/1980 | Itoh et al. |
| 4,290,943 | 9/1981 | Birr ..................................... 530/334 |
| 4,701,304 | 10/1987 | Horn et al. ....................... 436/89 X |
| 4,755,558 | 7/1988 | Kalbag ............................. 530/334 X |

FOREIGN PATENT DOCUMENTS 0097994 1/1984 European Pat. Off.
8603494 6/1986 World Int. Prop. O.

OTHER PUBLICATIONS

Wissman, H. et al., "Peptide Synthesis using Propylphosphonic Acid Anhydride as Coupling Agent" Chemical Abstracts 98, 726 (1983).

Teetz, V. et al., "Synthesis and Biological Properties of B1-3,5-diiodo-tyrosine" Chemical Abstracts 88, 612 (1978).

Kaiser et al., Analytical Biochemistry 34, 1970, pp. 595-598.

Scouten, "Solid Phase Biochemistry", John Wiley & Sons, New York, 1983, pp. 507-534.

"Continuous flow methods in organic synthesis", R. C. Sheppard, Chemistry in Britain, May 1983, pp. 402, 405, 407, 410, 411, 413 and 414.

"Solid Phase Peptide Synthesis using $N_\alpha$–Fluorenylmethoxycarbonylamino Acid Pentafluorophenyl Esters", E. Atherton and R. C. Sheppard, J. Chem. Soc., Chem. Commun., 1985, pp. 165 and 166.

Primary Examiner—Robert J. Warden
Assistant Examiner—Jeffrey R. Snay
Attorney, Agent, or Firm—Poms, Smith, Lande & Rose

[57] ABSTRACT

A monitoring method for application in solid phase peptide synthesis. In one aspect, the synthesis starts with an amino acid residue protected by an N-alpha-amino protecting group and involves the steps: (a) removing the N-alpha-amino protecting group to obtain an N-alpha-amino group, (b) adding an amino acid residue protected by an N-alpha-amino protecting group, via a peptide bond, to the N-alpha-amino group obtained in step (a) by use of a reactive protected amio acid derivative, and (c) repeating steps (a) and (b). The reaction system includes 3-hydroxy-1,2,3-benzotriazin-4(3H)-one or a derivative thereof; and the color of the reaction system or of a component thereof is monitored during the synthesis.

18 Claims, 2 Drawing Sheets

MONITORING METHOD FOR THE SYNTHESIS OF A LINEAR CONBINATION OF AMINO ACID RESIDUES

TECHNICAL FIELD

This invention relates to a method of monitoring the synthesis in particular (but not exclusively) by a solid phase technique of a linear combination of amino acid residues, and in particular to an optical monitoring technique which facilitates recirculating flow synthesis methods and automation of the synthesis procedure, and to such methods and procedures including the optical monitoring technique.

The solid phase synthesis of a linear combination of amino acid residues, linked via peptide bonds, generally starts with an amino acid residue covalently linked to a support and protected by an N-alpha-amino protecting group, and involves the steps:
 (a) removing the N-alpha-amino protecting group to obtain an N-alpha-amino group,
 (b) adding an amino acid residue protected by an N-alpha-amino protecting group, via a peptide bond, to the N-alpha-amino group obtained in step (a) by use of a reactive protected amino acid derivative and, where necessary, a catalyst, and
 (c) repeating steps (a) and (b) until the desired linear combination has been obtained.

BACKGROUND ART

Traditionally, such solid phase peptide synthesis has been carried out using t-butoxycarbonyl (boc) amino-acids activated in situ with an equivalent amount of dicyclohexyl-carbodiimide (DCCD). A significant advance was the introduction of preformed Boc and fluorenyl-mehtoxycarbonyl (Fmoc) amino-acid anhydrides in both polystyrene- and polyamide-based solid phase synthesis, avoiding contact of the reactive resin-bound amino group with the activating reagent. Acylation reactions are rapid, especially in polar media such as dimethylformamide.

Activated esters have also been used from time to time in solid phase synthesis but reaction rates may be low even in the presence of catalysts. Again polar reaction media are preferred, particularly in polyamide-based synthesis since this resin support is totally compatible with a wide range of aprotic polar and non-polar organic solvents. A particular synthesis method is disclosed in International Patent Publication No. WO86/03494, this method involving the use of activated Fmoc-amino-acid derivatives in which the acyl group used to form the peptide bond is activated as a pentafluorophenyl ester.

We have investigated the use of alternative activating agents in peptide synthesis, one of which is the compound:

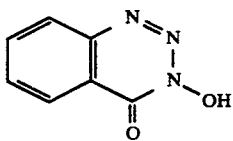

(I)

This compound is properly described as 3-hydroxy-1,2,3-benzotriazin-4(3h)-one; derivatives thereof are described by Koenig and Geiger in Chemische Berichte 1970, 103, 2034. Authors have used several ring numbering systems in the past and this has led to the use of several different names for this compound. For example, Koenig and Geiger (ibid.) describe the compound as 3-hydroxy-4-oxo-3,4-dihydro-1,2,3-benzotriazine and we ourselves described this compound in our U.K. Patent Application No. 86025866 as 1-oxo-2-hydroxy-dihydrobenzotriazine (DHBT). For ease of reference, this compound will be referred to hereinafter as "DHBT".

There is a ned to develop a fully automated system for synthesizing macromolecules such as peptides. In current so-called automated or semi-automated techniques, equipment is used in which control of the necessary liquid transfer operations, and consequently control of reaction times, is effected by somewhat inflexible computer software. This problem is an important one in peptide synthesis because rates of reaction can vary significantly as the synthetic procedure progresses and the length of the peptide chain increases. Reduced reaction rates can arise because of steric factors or, more seriously, because of sequence-dependent aggregation effects within the resin matrix in solid phase synthesis. These latter effects are generally unpredictable in their onset and can lead to failure of the desired synthesis reaction. Hitherto it has not been possible to provide automated synthesis apparatus or automated synthesis methods in which optimum reaction times can be determined for nay given reaction step in the course of a synthesis operation. After one such determination, it may be possible for the apparatus to be programmed to operate in accordance with the reaction times thus obtained.

Accordingly, there is a need for a motoring technique which is amenable to use in automated peptide synthesis in order to overcome the problems described above.

SUMMARY OF THE INVENTION

An object of the present invention is to provide a method of monitoring the progress of a synthesis of a linear combination of amino acid residues by an optical, e.g. photometric, method. This is attained by the method according to the present invention in that amino acids having an N-alpha-amino protecting group, e.g. Fmoc-amino-acid derivatives, are used in the synthesis; in that the reaction system includes DHBT, either in free or combined form; and in that the color of the reaction medium - e.g. solution or solid phase, or a portion of one thereof - is monitored during the synthesis.

The present invention provides, in a second aspect, a method of solid phase synthesis of a linear combination of amino acid residues, linked via peptide bonds, starting with an amino acid residue covalently linked to a support and protected by an N-alpha-amino protecting group, comprising the following steps:
 (a) removing the N-alpha-amino protecting group to obtain an N-alpha-amino group,
 (b) adding an amino acid residue protected by a N-alpha-amino protecting group, via a peptide bond, to the N-alpha-amino group obtained in step (a) by use of a reactive protected amino acid derivative and, when necessary, a catalyst, and
 (c) repeating steps (a) and (b) until the said linear combination has been obtained, characterized in that the reaction system includes 3-hydroxy-1,2,3-benzotriazin-4(3h)-one or a derivative thereof; and in that progress of the acylation reaction (step (b))

is monitored by observing the color of the reaction system or of a component thereof.

The monitoring method of the present invention facilitates the use of recirculating flow conditions in peptide synthesis.

According to a third aspect of the present invention, there is provided apparatus for the automated solid phase synthesis of peptides, which is characterized in that it includes means for monitoring the color of the reaction solution or of the solid phase or of a portion of one thereof during progress of the reaction. In one embodiment, the apparatus includes: (i) a column for receiving particles including a polyamide resin on which the solid phase synthesis is to take place; (ii) a light source disposed on one side of said column; (iii) a focusing arrangement disposed adjacent said column and opposite said light source; (iv) a photometer positioned to receive light focused by said focusing arrangement; and (v) a microprocessor programmed to respond to the output of said photodetector and to control the synthesis procedure in response thereto.

The preferred solvents for use in the methods of this invention are aprotic polar solvents, although aprotic non-polar solvents (e.g., tetrahydrofuran) and protic polar solvents may sometimes be of use.

In the solid phase synthetic methods of this invention, the preferred solid phase is a polyamides.

We have found that DHBT esters of Fmoc-amino acids are easily prepared and are generally stable crystalline solids most of which may be stored at low temperature for long periods without significant decomposition.

Advantageously, the reactive protected amino acid derivative has the acyl group which is used to form the peptide bond activated as a derivative (e.g. an ester, acid chloride or azide, preferably an ester) of 3-hydroxy-1,2,3-benzotriazin-4(3h)-one (i.e. a DHBT ester). These derivatives may be produced in situ by the addition of DHBT to the reaction medium. For example, the DHBT ester may be obtained by a transesterification reaction using DHBT and a protected amino acid in which the acyl group which is used to form the peptide bond is in the form of a pentafluorophenyl ester.

It is generally preferred to use, as the protected amino acid derivative, an ester of an Fmoc-amino acid. Likewise, the preferred aprotic solvent is dimethylformamide.

The color of the reaction system or of a component thereof is advantageously monitored photometrically, preferably at about 440 nm. It may be the color of the solid phase which is monitored, or that of the reactive solution, depending on the conditions used for synthesis. If the reactive solution is basic, the yellow coloration appears in the liquid phase; if not, it appears on the solid phase. In one embodiment, 3-hydroxy-1,2,3-benzotriazin-4(3h)-one is added to a portion of the solid phase support which has been removed from The reaction system, and the color of the removed portion of solid phase support is monitored.

During step (b) of the solid phase synthetic reaction sequence outlined above in which the reactive protected amino acid derivative has the acyl group which is used to form the peptide bond activated as a DHBT ester, the DHBT ester residue reacts with the growing peptide chain and the N-hydroxy compound enters solution. We have found that, during this acylation reaction, a transient bright yellow coloration appears on the resin during the acylation reaction, although the solution remains colorless in the absence of dissolved base. The yellow coloration diminishes as the acylation reaction proceeds and, with a base-free solution, the resin returns to its initial off-white shade. This yellow coloration is believed to involve ionization of liberated DHBT by resin bound amino groups. As the acylation reaction proceeds, the resin bound amino groups react until there is no coloration remaining. If a basic reaction medium is used, for example a reaction solution having as solvent dimethylformamide and including a base, e.g. N-methylmorpholine, diisopropylethylamine, piperidine or N-ethylmorpholine, the yellow color is produced in the solution instead of on the solid phase. It is believed that this coloration is due to ionization of the liberated N-hydroxy compound in the basic solution. The extent of the coloration in either case can be observed photometrically in the region of 440 nm. Step (b) of the reaction sequence is considered to be complete when there is no further color change, or when the rate of change of color (e.g. as observed photometrically) decreases or approaches zero, e.g. when the photometric curve forms a plateau or a smoothly increasing line (since traces of residual piperidine may result in a gradually increasing UV absorption), although it is advisable to maintain reaction conditions for somewhat longer than is necessary to reach this "steady state".

BRIEF DESCRIPTION OF THE DRAWINGS

The invention will now be described in more detail in the following Examples. Reference is made, in Example 4, to the accompanying drawings, in which.

DETAILED DESCRIPTION

Figure 1:
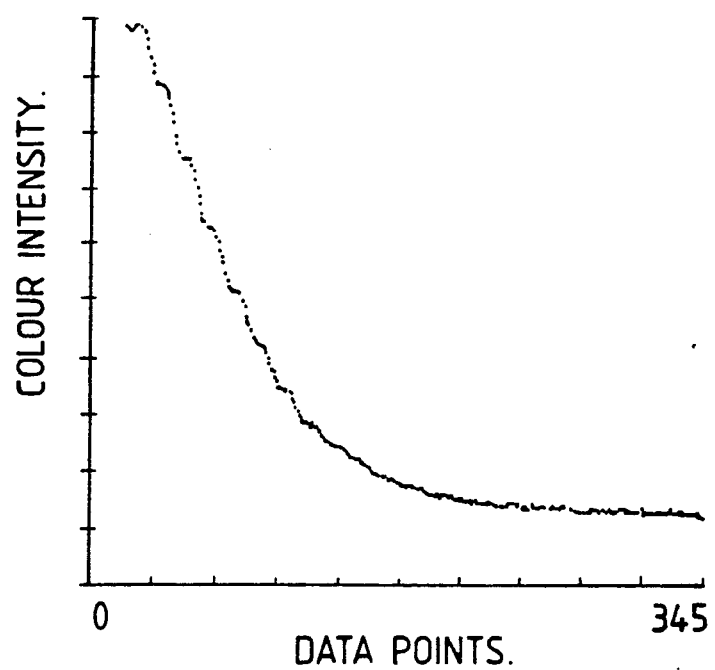
FIG. 1 is a plot of resin color intensity versus time for a model coupling of Fmoc.Val.ODHBT with isoleucyl-rein in which 345 readings were collected at 12 second intervals, the analog data being digitized and plotted directly.

DHBT esters prepared with the aid of dicylochexyl-carbodiimide may be accompanied by the azidobenzoate product:

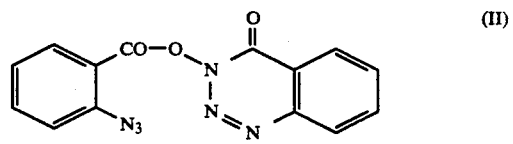

(II)

Traces of this product may easily be detected by hplc (e.g. Fmoc.Gly.ODHBT and the above produce emerge at 26.8 and 24.3 min respectively on Aquapore 300 using a gradient of 0%–100% B in 40 min). All Fmoc-amino acid derivatives should therefore be rigorously purified before use in peptide synthesis since the above azidobenzoate is an effective chain terminating agent. In some syntheses, traces of contaminating azidobenzoyl peptides have been detected. Formation of the above azidobenzoate is minimized by preparation of the active esters in a non-polar solvent (tetrahydrofuran) rather than in polar dimethylformamide, although the latter is to be preferred for the less soluble, side chain reactive amino-acids, asparagine and gluatamine. Almost complete suppression of the above azidobenzoate product is obtained by preformation of the Fmoc-amino acid —DCCI adduct 4 min before addition of DHBT.

For a test case the very different acyl carrier protein 64–74 sequence

$$\text{H.Val.Gln.Ala.Ala.Ile.Asp.Tyr.Ile.Asn.Gly.OH} \quad \text{(III)}$$
$$1 \hspace{6.5em} 10$$

was selected. Earlier attempts to assemble this sequence using p-nitrophenyl esters in the presence of catalyst 1-hydroxybenzotrilzole were quite unsuccessful, although excellent syntheses were achieved using symmetrical anhydrides. Excellent syntheses were also achieved using pentafluorophenyl esters in accordance with the method described in International Patent Publication WO 86/03494. The technique used in each of the following Examples was the continuous flow variant of the Fmoc-polyamide procedure as described by R. C. Sheppard in Chem. Br., 1983, 19, 402.

Fmoc-amino-acid DHBT esters were prepared by conventional synthetic methods.

EXAMPLE 1

The polydimethylacrylamide resin

(IV)

HOCH$_2$—⟨⟩—OCH$_2$CO.Nle-polydimethylacrylamide was supported in rigid, macroporous kieselguhr particles and was functionalized with an internal reference norleucine residue and with the acid-labile p-alkoxybenzyl alcohol linkage agent as known per se.

The acylation reactions were carried out using an excess of amino acid DHBT ester dissolved in dimethylformamide. This solution was recirculated over the resin. Esterification of the C-terminal Fmoc-glycine residue utilized the pentafluorophenyl ester derivative in the presence of 4-dimethylamino-pyridine catalyst. With Fmoc-glycine pentafluorophenyl ester (5 equiv.) in the presence of 4-dimethylaminopryidine (1 equiv.), esterification was complete in 1–2 h. All peptide bond-forming reactions utilized the appropriate Fmoc-amino acid DHBT ester (4 equiv.) in dimethylformamide. Urea was added to the reaction mixture for incorporation of the final valine residue (see below). Fluroenylmethoxycarbonyl groups were cleaved by 20% piperidine/dimethylformamide.

In this Example, the progress of the synthesis was followed by observing persistence of the initial yellow coloration of the column, although for safety acylation times were set considerably longer. The following approximate times were noted for fading of the resin to its original off-white state with actual total reaction times in parentheses: Asn-Gly, 15 min (35 min); Ile-Asn, 30 min (65 min); Tyr-Ile, 18 min (60 min); Asp-Tyr, 10 min (40 min); Ile-Asp, 15 min (40 min); Ala-Ile, 10 min (40 min); Ala-Ala, 10 min (40 min); Gln-Ala, 30 min (130 min); Val-Gln; 20 h (24 h). The exceptionally long reaction time noted for the final valine residue is in agreement with previous experience. After the addition of glutamine, photometric evidence for storing association of the peptide chains within the resin matrix was provided by slower release of dibenzofulvene-piperidine adduct during deprotection steps.

The completed decapeptide was cleaved from the resin with 95% trifluoroacetic acid; detachment was 92% complete as judged by the glycine:norluecine analysis of residual resin. The unpurified decapeptide had the following amino-acid analysis: Gly, 1.00; Asp, 1.91; Ile, 1.80; Tyr, 0.91; Ala, 1.87; Glu, 0.96; Val, 0.94. After hplc purification as described by E. Atherton and R. C. Sheppard in J. Chem. Soc. Chem. Comm., 1985, 165, the amino-acid analysis was Gly, 1.00; Asp, 1.96; Ile, 1.92; Tyr, 0.95; Ala, 2.04; Glu, 0.98; Val, 0.98.

A second synthesis of the same sequence, identical in procedure to the synthesis described above except that it involved using only two equivalents of DHBT ester except for the final valine (4 equiv, no urea), also gave satisfactory results.

EXAMPLE 2

Using techniques and reaction conditions analogous to those of Example 1, satisfactory synthesis of the following peptide sequences have been achieved:

H.Val.Leu.Arg.Asn.Pro.Asp.Gly.Glu.Ile.Glu.Lys.Gly.OH  (V)

H.Ile.Ala.Glu.Ile.Gly.Ala.Ser.Leu.Ile.Lys.His.Trp.OH  (VI)

H.Gly.Lys.Lys.Lys.Cys(Acm).Ser.Glu.Ser.—  (VII)
—Ser.Asp.Ser.Gly.Ser.Tyr.Gly.OH

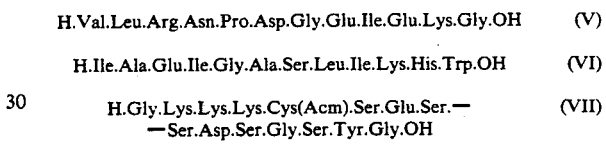

EXAMPLE 3

In a second synthesis of the sequence described in Example 1, the end points of the acylation reactions were determined using photometric observation of the resin color at 440 mm. The results obtained were generally consistent with those obtained by visual estimation, except that both isoleucine residues gave approximately equal (36 min, 40 min) times for complete decoloration (see below). Essentially, light from a low voltage quartz-halogen source was focused onto a bed of the translucent resin support approximately 4 mm in thickness, and the diffused, transmitted light refocused through a 440 nm narrow band pass filter onto a photo transistor detector. A magnetically operated shutter mechanism was used to limit the exposure of the resin to the light source. The detector output was digitized, sampled, and processed directly by a controlling microprocessor. A typical real time plot of the fall in absorption to a steady baseline state as acylation proceeds is shown in FIG. 1 of the accompanying drawings.

The fluctuation in the descending trace of FIG. 1 are due to absorption by the recirculating acylating species:

(VIII)

Figure 2:
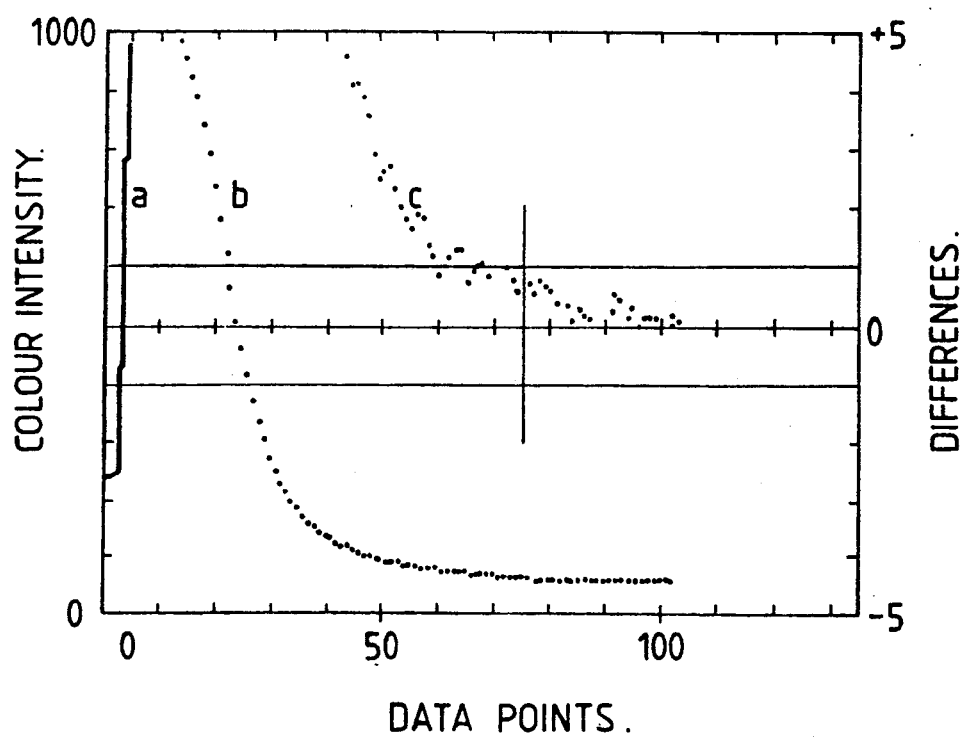
FIG. 2 shows the coupling of Fmoc.Asn.ODHBT with glycyl-resin in the synthesis of acyl carrier protein decapeptide residues 65–74 (compound III below); in this Figure, the vertical line marks the computer-determined end point.
Figure 3:
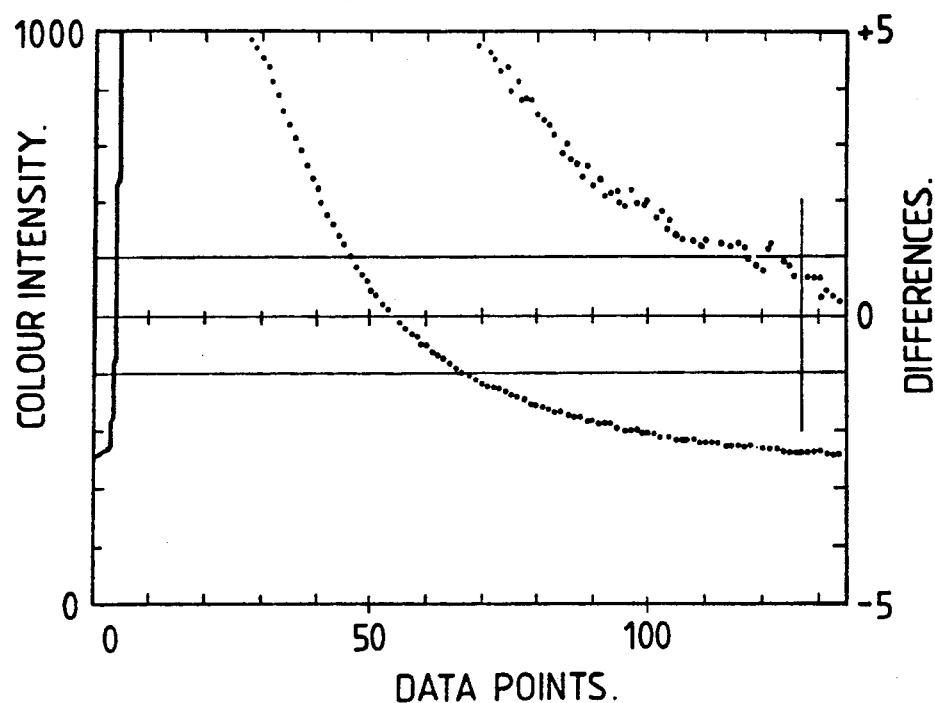
FIG. 3 illustrates the coupling of Fmoc.Ile.ODHBT with asparaginylgylcyl-resin.
Figure 4:
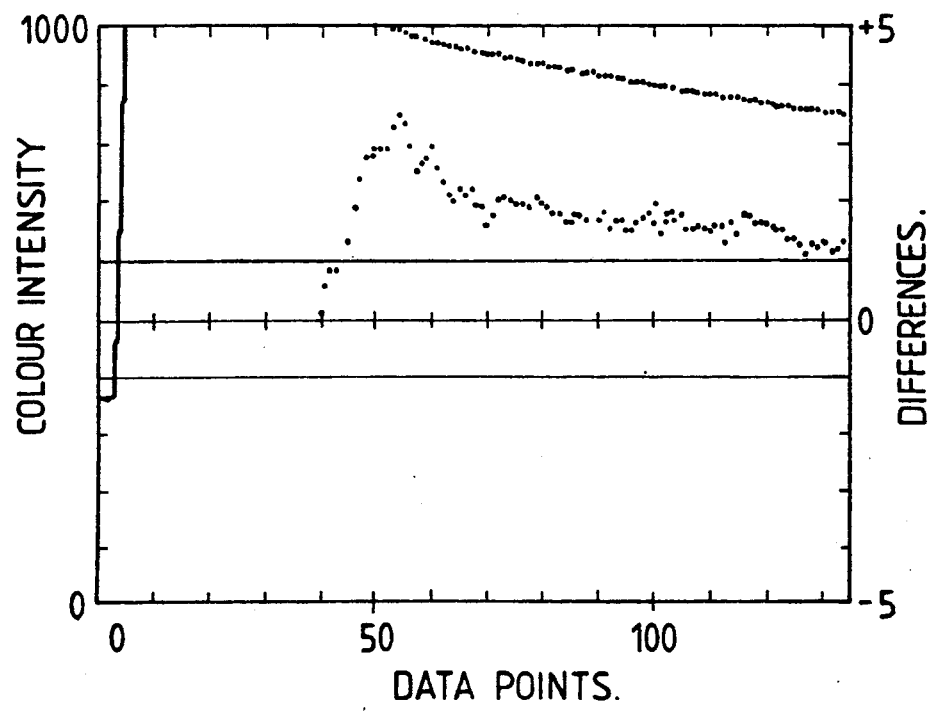
FIG. 4 illustrates the final step (coupling of Fmoc.-Val.ODHBT to N-terminal glutamine) in the assembly of the decapeptide.

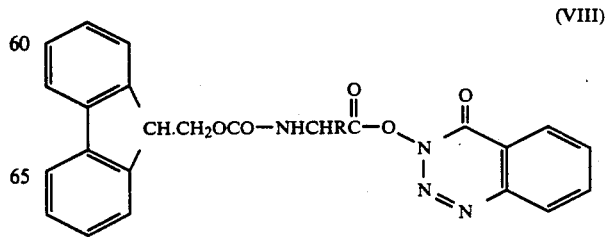

and by ionized DHBT in solution. They can be simply removed by averaging the data over a time corresponding approximately to the recirculation period. FIGS. 2-4 show results obtained during actual peptide synthesis using the Fmoc-polyamide continuous flow procedure described by A. Dryland and R. C. Sheppard in J. Chem. Soc. Perkin. I, 1986, 125. Curve (a) of FIG. 2 shows sample addition, curve (b) shows fall in absorption as acylation proceeds and curve (c) shows the difference between successive readings. These last are plotted on the very much expanded vertical scale of −5 to +5, with the horizontal delimiters shown set at −1 and +1. In this Example, acylation was considered complete when 5 successive difference readings lay between these limits. The acylation step was automatically terminated after an additional 10 minute period.

The decapeptide sequence (III) synthesized contains normal and sterically hindered residues and its synthesis involves one step at which massive hindrance due to internal aggregation occurs. Two fold excess of Fmoc-amino acid exters (VIII) were used for each peptide bond-forming step except the last (see below). The controlling microcomputer was programmed to collect a maximum of 135 readings at 20 sec intervals. FIG. 2 is the record for formation of the first peptide bond (asparagine to glycine). The ned point was detected automatically at 23.2 min. The following sterically hindered isoleucine residue (FIG. 3) was slower at 40 min, as expected. Successive residues gave end points at 19.4 min (Tyr), 17.4 min (Asp), 35.8 min (Ile), 17.8 min (Ala), 17.8 min (Ala), and 21.8 min (Gln). The last acylation step (valine to glutamine) is known from previous experience to be exceptionally slow due largely to internal aggravation within the resin matrix. A four fold excess of the activated ester was used. It was clearly incomplete (FIG. 4) at the end of the time set for data collection (45 min). The count down was suspended manually and the reaction allowed to proceed overnight. After deprotection and cleavage (92%) from the resin, the crude decapeptide (found: Val, 0.93; Glu, 0.99; Ala, 1.92; Ile, 1.64; Asp, 2.01; Tyr, 0.93; Gly 1.00) obtained was of good quality with an hplc profile comparable to that of previous, manually controlled synthesis. An equally satisfactory synthesis of the following nineteen residue part sequence of the calcium binding protein endoplasmin has since been achieved in similar manner:

$Gly_{103}$ 40 min (15 min); $Ile_{102}$ 40 min (20 min); $Glu_{101}$ 30 min (15 min); $Gly_{100}$ 30 min (12 min); $Asp_{99}$ 40 min (20 min); $Pro_{98}$ 40 min (12 min); $Asn_{97}$ 90 min (90 min); $Arg_{96}$ 210 min (120 min); $Leu_{95}$ 75 min (15 min); $Val_{94}$ 50 min (20 min). Thus H-Gly-Handle-Nle-Resin (2 g, 0.20 mmol) was acylated with Fmoc-amino acid-DHBT ester (0.62 mmol, 3 eqv) dissolved in 0.5% DIPEA in DMF (8 ml) in an automatic peptide synthesizer. After each acylation the column was washed for 15 min and the Fmoc-group was removed by a 10 min flow with 20% piperidine in DMF. The absorption of the effluent was monitored at 330 nm. The final resin was treated as described in Example 1. The peptide on the resin was hydroxlyzed and subjected to amino acid analysis: (Found Gly, 2.00; Asp, 1.90; Glu, 2.00; Pro, 1.01; Val, 0.91; Ile, 0.94; Leu, 0.92; Nle, 1.02; Lys, 1.02; Arg 0.93). The peptide was cleaved off the resin by a 24 treatment with TFA (10 ml) containing 5% phenol. The product was isolated by filtration and evaporation in vacuo followed by a threefold extraction with diethyl ether and lyophilization from water (3 ml).

The peptide was analyzed by Hplc and peaks were collected and analyzed by amino acid analysis using a isocratic elution at 0% buffer B followed by a linear gradient from 0% to 50% buffer B in 38 min. Of the observed peaks, only those at 18 min and at 19.2 min contained peptide and both analyzed correctly.

(b) Assembly of Penecilianse fragment 1-12

HO-Handle-Nle-Resin (1.4 g, 0.15 mmol) was acylated with Fmoc-Trp-O-DHBt (342 mg, 0.6 mmol) and DMAP (20 mg, 0.16) mmol in DMF (7 ml) by recirculation on an automatic continuous flow peptide synthesizer. After 1.3 h the mixture was washed out and the residual hydroxyl groups was end capped with acetic anhydride (100 microliter 1 mmol) and DMAP (30 mg, 0.25 mmol). The resin was washed with DMF and the Fmoc-group was removed with 20% piperidine. Monitoring the absorption of the effluent at 312 nm showed the incorporation of Irp to be only 20%. The assembly was carried out as described in Example 1, monitoring the reaction by transmission of light at 440 nm through a small layer of resin (1.5 mm in a flow cell and measurement of the absorption due to the DHBt-OH, depotanted by residual amino groups on the resin. The reactions were considered complete when the readings did not change more than 1% of the maximal absorption.

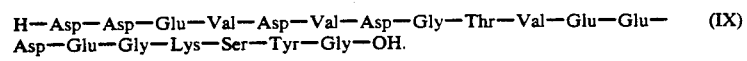

H—Asp—Asp—Glu—Val—Asp—Val—Asp—Gly—Thr—Val—Glu—Glu— (IX)
Asp—Glu—Gly—Lys—Ser—Tyr—Gly—OH.

EXAMPLE 4

The synthesis of a number of additional peptides using the method of the invention will now be described.

(a) Assembly of Escherichia coil K88 ad fimbrial protein fragment 94-105

The peptide H-Val-Leu-Arg-Asn-Pro-Asp-Gly-Glu-Ile-Glu-Lys-Gly-OH was assembled using the techniques described in Example 1 but with the presence of 1.5% diisopropyl ethyl amine in the DMF (at all stages expect for the acylation with $Arg_{96}$ and $Asn_{97}$). The color yield in the solution was measured at 460 nm and the result was used to determine the reaction times. The acylation times were (approximate observed reaction times are given in parenthesis): $Lys_{104}$ 40 min (15 min);

The acylation times were (observed reaction times are given in parenthesis): $His_{11}$ 50 min (12 min); $Lys_{10}$ 45 min (12 min); $Ile_9$ 50 min (20 min); $Leu_8$ 25 min (10 min); $Ser_7$ 25 min (10 min); $Ala_6$ 27 min (10 min); $Gly_5$ 25 min (10 min); $Ile_4$ 90 min (30 min); $Glu_3$ 70 min (20 min); $Ala_2$ 80 min (25 min); Ile, 150 min. In the four last acylations the reaction was carried out in the presence of 1% urea. Each acylation was followed by a 15 min wash with DMF and a 10 min flow with 20% piperidine in DMF. The cycle was concluded with a 25 min was with DMF. During the Fmoc cleavages the absorption of the effluent at 312 nm was monitored. The final product was washed and dried as described for the Acp fragment and an aliquot of the resin was hydrolyzed and subjected to amino acid (Found: Gly, 1.00; Ser, 0.82; Glu, 1.02; Ala, 2.01; Ile, 2.81; Leu, 0.97; Nle, 4.30; His, 0.99; Lys, 0.99).

The peptide was cleaved off the resin (70 mg) by treatment for 1.5 h nitrogen purged with TFA (3 ml) containing 3% anisole and 1% ethane dithiol. The resin was filtered off and washed with heat TFA. The solvents were removed by evaporation in vacuo and after a three fold extraction with diethyl ether the product was dried with a stream of nitrogen and analyzed by Hplc eluting isocratic for 2 min with 20% buffer B followed by a linear gradient of 20%-50% B in 30 min. The peaks eluting at 13.3 and at 15.5 min both analyzed for the correct sequence, but the peak at 15.5 min coincided with a purified penecilianse fragment 1-12 prepared previously by the Pfp ester method.

(c) Assembly of Protein P 16 fragment 13-27

The peptide H-Gly-Lys-Lys-Lys-Cyc(Acm)-Ser-Glu-Ser-Ser-Asp-Gly-Ser-Tyr-Gly-OH was assembled on H-Gly-Handle-Nle-Resin (1.4 g, 0.154 mmol) using a four fold excess of Fmoc-amino acid-DHBt esters (0.616 mmol). The progress of reactions during the acylations were followed by measuring the absorbance at 440 nm of light passed through a 1 mm layer of resin in the bottom of the column. The reactions were terminated when the change in absorbance ceased. The acylation times were: (observed reaction times are given in parenthesis). $Try_{26}$ 50 min (10 min); $Ser_{25}$ 50 min (10 min); $Gly_{24}$ 50 min (5 min); $Ser_{23}$ 50 min (15 min); $Asp_{22}$ 50 min (10 min); $Ser_{21}$ 50 min (10 min); $Ser_{20}$ 50 min (15 min); $Glu_{19}$ 50 min (10 min); $Ser_{18}$ 50 min (17 min); $Gys_{17}$ 50 min (14 min); $Lys_{16}$ 50 min (20 min); $Lys_{15}$ 60 min (50 min); $Lys_{14}$ 240 min (90 min); $Gly_{13}$ 60 min (30 min). After each acylation cycle the resin was flowed (2.2 ml/min) with DMF for 15 min and the Fmoc-group was removed with 10 min flow with 20% piperidine in DMF. The cycles were completed by a 25 min flow with DMF. the final product was washed successively with DMF, t-amyl alcohol, glacial acetic acid, t-amyl alcohol, DMF, and diethyl ether and the resin was dried in vacuo. The resin was hydrolyzed and subjected to amino acid analysis (Found: Gly, 3.00; Asp, 1.02; Ser, 4.17; Glu, 1.00; Cys, Not Integrated; Nle, 1.091; Tyr, 0.90; Lys, 2.96.

The peptide was cleaved off the resin (40 mg) by treatment with 95% aqueous TFA (1 ml) for 1.6 h. The resin was removed and the TFA was evaporated. The residue was extracted 3 times with diethyl ether (25 ml) and was dried in vacuo.

The product was analyzed by Hplc (c.f. FIG. 8) eluting isocratic with 5% of buffer B for 2 min followed by a linear gradient of 5%-25% buffer B in 18 min. The major peak at 9 min and the minor at peak at 10.8 min were collected and subjected to amino acid analysis. The former analyzed for protein P 16 fragment 13-27 whereas in the latter a lysine was missing.

The examples given above provide a basis for pure automation of solid phase synthesis operated under continuous flow conditions. No additional reagents, resin removal, or other interferences with the synthetic procedure is required. The data may produced, displayed to the operator and computer-interpreted as the reactions are proceeding and at a time when remedial action can be taken automatically or manually if required. There can be substantial speeding of synthesis, but the main importance lies in the detection of particularly slow steps which with preset reaction times could otherwise cause the synthesis to fail.

We claim:

1. A method of solid phase synthesis of a linear combination of amino acid residues linked via peptide bonds, said method comprising the steps of:
    (a) covalently linking an amino acid residue to a solid support to form a synthesis medium wherein said amino acid residue is protected by an N-alpha-amino protecting group;
    (b) removing the N-alpha-amino protecting group from said amino acid residue in said synthesis medium to obtain an N-alpha-amino group;
    (c) conducting an acylation reaction in said synthesis medium by adding a subsequent amino acid residue protected by a N-alpha-amino protecting group, via a peptide bond, to the N-alpha-amino group obtained in step (b) by use of a reactive protected amino acid derivative; and
    (d) repeating steps (b) and (c) until the said linear combination has been obtained, wherein the improvement comprises continually monitoring the progress of the acylation reaction in said synthesis medium by observing the color of the synthesis medium without removing any part of the synthesis medium therefrom, providing 3-hydroxyl-1,2,3-benzotriazin-4(3H)-one or a derivative thereof as said reactive protected amino acid derivative, wherein the color of said synthesis medium which is observed is provided by said 3-hydroxyl-1,2,3-benzotriazin-4(3H)-one or derivative thereof and wherein said acylation reaction is carried out in a reaction solution which includes said reactive protected amino acid derivative.

2. A method according to claim 1, wherein said solid support is a polyamide support.

3. A method according to claim 1, wherein the acylation reaction is effected by recirculating the reactive solution.

4. A method according to claim 1, wherein the reaction solution contains a component selected from the group consisting of N-methylmorpholine, diisopropylethylamine, piperidine and N-ethylmorpholine.

5. A method according to claim 1 further including the step of adding a catalyst concurrent with the adding step in step (c).

6. A method according to claim 1, wherein, in said step (c), said reactive protected amino acid derivative is a derivative of 3-hydroxyl-1,2,3-benzotriazin-4(3H)-one and has an acyl group which is used to form the peptide bond.

7. A method according to claim 6, wherein said reactive protected amino acid derivative is an ester derivative of 3-hydroxyl-1,2,3-benzotriazin-4(3H)-one.

8. A method according to claim 6, wherein said reactive protected amino acid derivative is an azide or acid chloride derivative of 3-hydroxyl-1,2,3-benzotriazin-4(3H)-one.

9. A method according to claim 6, wherein said reactive protected amino acid derivative is an ester of an Fmoc-amino acid.

10. A method according to claim 6, wherein said derivative of 3-hydroxyl-1,2,4-benzotriazin-4(3H)-one is produced in situ by the addition of 3-hydroxyl-1,2,3-benzotriazin-4(3H)-one to the reaction solution.

11. A method according to claim 10, wherein said reactive protected amino acid derivative is an ester of 3-hydroxyl-1,2,4-benzotriazin-4(3H)-one obtained by a transesterification reaction using a protected amino acid in which the acyl group which is used to form the peptide bond is in the form of a pentafluorophenyl ester.

12. A method according to claim 1, wherein the color of the synthesis medium is monitored photometrically.

13. A method according to claim 12, wherein the color is monitored photometrically at about 440 nm.

14. A method according to claim 1, wherein the reaction solution includes an aprotic solvent.

15. A method according to claim 14, wherein said aprotic solvent is a polar solvent.

16. A method according to claim 15, wherein said solvent is dimethylformamide.

17. A method according to claim 14, wherein said aprotic solvent is a non-polar solvent.

18. A method according to claim 17, wherein said solvent is tetrahydrofuran.

* * * * *